(12) United States Patent
Hauck et al.

(10) Patent No.: US 7,670,297 B1
(45) Date of Patent: Mar. 2, 2010

(54) CHAMBER MAPPING SYSTEM

(75) Inventors: John A. Hauck, Shoreview, MN (US); Eric J. Voth, Maplewood, MN (US); Clifford B. Miller, Bridgewater, NJ (US)

(73) Assignee: St. Jude Medical, Atrial Fibrillation division, Inc., St. Paul, MN (US)

( * ) Notice: Subject to any disclaimer, the term of this patent is extended or adjusted under 35 U.S.C. 154(b) by 2005 days.

(21) Appl. No.: 09/107,371

(22) Filed: Jun. 30, 1998

(51) Int. Cl.
*A61B 5/02* (2006.01)
*A61B 5/0402* (2006.01)

(52) U.S. Cl. .................. 600/508; 600/374; 600/523

(58) Field of Classification Search .............. 600/374, 600/508, 523, 527, 407, 416, 421, 424, 425, 600/450; 128/916, 922
See application file for complete search history.

(56) References Cited

U.S. PATENT DOCUMENTS

| | | | |
|---|---|---|---|
| 3,954,098 A | 5/1976 | Dick et al. |
| 4,173,228 A | 11/1979 | Van Steenwyk et al. |
| 4,304,239 A | 12/1981 | Perlin |
| 4,380,237 A | 4/1983 | Newbower |
| 4,431,005 A | 2/1984 | McCormick |
| 4,444,195 A | 4/1984 | Gold |
| 4,478,223 A | 10/1984 | Allor |
| 4,559,951 A | 12/1985 | Dahl et al. |
| 4,572,186 A | 2/1986 | Gould et al. |
| 4,572,206 A | 2/1986 | Geddes et al. |
| 4,573,473 A | 3/1986 | Hess |
| 4,613,866 A | 9/1986 | Blood |
| 4,628,937 A | 12/1986 | Hess et al. |
| 4,641,649 A | 2/1987 | Walinsky et al. |
| 4,649,924 A | 3/1987 | Taccardi |
| 4,674,518 A | 6/1987 | Salo |
| 4,697,595 A | 10/1987 | Breyer et al. |
| 4,699,147 A | 10/1987 | Chilson et al. |
| 4,706,670 A | 11/1987 | Andersen et al. |
| 4,721,115 A | 1/1988 | Owens |
| 4,777,955 A | 10/1988 | Brayton et al. |
| 4,821,731 A | 4/1989 | Martinelli et al. |
| 4,840,182 A | 6/1989 | Carlson |
| 4,890,623 A | 1/1990 | Cook et al. |
| 4,898,176 A | 2/1990 | Petre |
| 4,898,181 A | 2/1990 | Kessler |
| 4,899,750 A | 2/1990 | Ekwall |
| 4,940,064 A | 7/1990 | Desai |
| 4,945,305 A | 7/1990 | Blood |
| 4,945,342 A | 7/1990 | Steinemann |
| 4,951,682 A | 8/1990 | Petre |
| 5,000,190 A | 3/1991 | Petre |
| 5,005,587 A | 4/1991 | Scott |
| 5,025,786 A | 6/1991 | Siegel |
| 5,029,588 A | 7/1991 | Yock et al. |
| 5,042,486 A | 8/1991 | Pfeiler et al. |

(Continued)

OTHER PUBLICATIONS

The QuickHull Algorithm for Convex Hulls; ACM Trans. on Mathematical Software, vol. 22 No. 4 see also www.acm.org/pubs/toc/Abstracts toms/ 235821.html.

(Continued)

*Primary Examiner*—Lee S Cohen
(74) *Attorney, Agent, or Firm*—Dykema Gossett PLLC

(57) ABSTRACT

A computational process for approximating and representing the shape of the interior of the heart is disclosed.

11 Claims, 4 Drawing Sheets

U.S. PATENT DOCUMENTS

| | | | |
|---|---|---|---|
| 5,054,492 | A | 10/1991 | Scribner et al. |
| 5,054,496 | A | 10/1991 | Wen et al. |
| 5,056,517 | A | 10/1991 | Fenici |
| 5,058,583 | A | 10/1991 | Geddes et al. |
| 5,081,993 | A | 1/1992 | Kitney et al. |
| 5,090,411 | A | 2/1992 | Higuchi |
| 5,158,092 | A | 10/1992 | Glace |
| 5,161,536 | A | 11/1992 | Vilkomerson et al. |
| 5,211,165 | A | 5/1993 | Dumoulin et al. |
| 5,220,924 | A | 6/1993 | Frazin |
| 5,228,442 | A | 7/1993 | Imran |
| 5,237,996 | A | 8/1993 | Waldman et al. |
| 5,255,678 | A | 10/1993 | Deslauriers et al. |
| 5,273,038 | A | 12/1993 | Beavin |
| 5,282,471 | A | 2/1994 | Sato |
| 5,295,484 | A | 3/1994 | Marcus et al. |
| 5,305,745 | A | 4/1994 | Zacouto |
| 5,323,781 | A | 6/1994 | Ideker et al. |
| 5,324,284 | A | 6/1994 | Imran |
| 5,325,860 | A | 7/1994 | Seward et al. |
| 5,341,807 | A | 8/1994 | Nardella |
| 5,345,936 | A | 9/1994 | Pomeranz et al. |
| 5,360,006 | A * | 11/1994 | Geiser et al. ............ 128/653.1 |
| 5,372,138 | A | 12/1994 | Crowley et al. |
| 5,377,678 | A | 1/1995 | Dumoulin et al. |
| 5,385,146 | A | 1/1995 | Goldreyer |
| 5,391,199 | A | 2/1995 | Ben-Haim |
| 5,409,000 | A | 4/1995 | Imran |
| 5,433,198 | A | 7/1995 | Desai |
| 5,458,126 | A * | 10/1995 | Cline et al. ............. 128/653.1 |
| 5,551,426 | A | 9/1996 | Hummel et al. |
| 5,553,611 | A | 9/1996 | Budd et al. |
| 5,558,091 | A | 9/1996 | Acker et al. |
| 5,588,432 | A | 12/1996 | Crowley |
| 5,601,084 | A * | 2/1997 | Sheehan et al. ............ 600/425 |
| 5,622,174 | A | 4/1997 | Yamazaki |
| 5,662,108 | A | 9/1997 | Budd et al. |
| 5,669,382 | A * | 9/1997 | Curwen et al. ............. 382/272 |
| 5,687,737 | A | 11/1997 | Branham et al. |
| 5,697,377 | A | 12/1997 | Witkampf |
| 5,701,897 | A | 12/1997 | Sano |
| 5,713,363 | A | 2/1998 | Seward et al. |
| 5,722,402 | A | 3/1998 | Swanson et al. |
| 5,738,096 | A | 4/1998 | Ben-Haim |
| 5,797,396 | A * | 8/1998 | Geiser et al. ................ 382/128 |
| 5,824,005 | A | 10/1998 | Motamedi et al. |
| 5,840,031 | A | 11/1998 | Crowley |
| 5,846,198 | A | 12/1998 | Killmann |
| 5,848,972 | A | 12/1998 | Triedman et al. |
| 5,871,019 | A * | 2/1999 | Belohlavek ................ 600/450 |
| 5,908,446 | A | 6/1999 | Imran |
| 6,004,269 | A | 12/1999 | Crowley et al. |
| 6,095,976 | A | 8/2000 | Nachtomy et al. |
| 6,603,996 | B1 | 8/2003 | Beatty et al. |

OTHER PUBLICATIONS

Arisi, G., et al., "Localization Of Ectopic Ventricular Focuses By Means Of A Diameter Multielectrode Catheter," *Advances in Electrocardiology*, Elsevier Science Publishers B.V. (Biomedical Division), Z. Antaloczy et al., editors, pp. 67-70 (1990).

Branham B., et al., "A System For Accurate Interactive 3-D Display Of Cardiac Electrical Activity," *Computers in Cardiology*, IEEE Computer Society Press 0276-6547/92, pp. 335-338 (Oct. 11-14, 1992).

Breyer, B. and Cikes, I., "Ultrasonically Marked Catheter—A Method For Positive Echographic Catheter Position Identification," *Med. & Biol. Eng. & Comput.*, 22:268-271 (May 1984).

Buckles, D., et al., "Computer-Enhanced Mapping Of Activation Sequences In The Surgical Treatment Of Supraventricular Arrhythmias," *PACE*, vol. 13, Part I, pp. 1401-1407 (Nov. 1990).

Cikes, I., et al., "Cardiac Catheterisation Guided By Ultrasound," *Journal of the American College of Cardiology*, vol. 3, No. 2, p. 564 (Feb. 1984).

Cikes, I. and Breyer, B., "Complete Cardiac Catheterisation Guided By Ultrasound," *European Heart Journal*, vol. 4 (suppl. E), p. 21 (1983).

Cikes, I., "Interventional Echocardiography," *5th Symposium on Echocardiology*, Rotterdam, Abstracts p. 38 (1983).

Cikes, I., et al., "Interventional Echocardiography," *Interventional Ultrasound*, 1st edition, chapter 25, Munksgaard, Copenhagen, pp. 160-168 (1985).

Cox, J., et al., "Surgery For Atrial Fibrillation," *Cardiac Surgery: State of the Art Reviews*, vol. 4, No. 1, pp. 207-217 (1990).

De Bakker, J., et al., "Endocardial Mapping By Simultaneous Recording Of Endocardial Electrograms During Cardiac Surgery For Ventricular Aneurysm," *Journal of American College of Cardiology*, vol. 2, No. 5, pp. 947-953 (Nov. 1983).

Derfus, D. and Pilkington, T., "Assessing The Effect Of Uncertainty In Intracavitary Electrode Position On Endocardial Potential Estimates," *IEEE Transactions on Biomedical Engineering*, vol. 39, No. 7, pp. 676-681 (Jul. 1992).

Derfus, D., et al., "Calculating Intracavitary Potentials from Measured Endocardial Potentials," *Annual International Conference of the IEEE Engineering in Medicine and Biology Society*, vol. 12, No. 2, p. 635 (1990).

Derfus, D., et al., "A Comparison of Measured and Calculated Intracavitary Potentials for Electrical Stimuli in the Exposed Dog Heart," *IEEE Transactions on Biomedical Engineering*, vol. 39, No. 11, pp. 1192-1206 (Nov. 1992).

Derfus, D. and Pilkington, T., "Effect Of Intracavitary Electrode Position On Endocardial Potential Estimates," *IEEE Engineering in Medicine & Biology Society 10th Annual International Conference*, pp. 185-186 (1988).

Desai, J., et al., "Orthogonal Electrode Catheter Array for Mapping of Endocardial Focal Site of Ventricular Activation," *PACE*, vol. 14, Part I, pp. 557-574 (Apr. 1991).

Downar, E., et al., "Endocardial Mapping of Ventricular Tachycardia in the Intact Human Ventricle: Evidence for Reentrant Mechanisms," *Journal of the American College of Cardiology*, vol. 11, No. 4, pp. 783-791 (Apr. 1988).

Durrer, D. and Van Der Tweel, L., "Spread of Activation in the Left Ventricular Wall of the Dog. II.: Activation Conditions at the Epicardial Surface," *American Heart Journal*, pp. 192-203 (Aug. 1953).

Fann, J., et al., "Endocardial Activation Mapping and Endocardial Pace-Mapping Using a Balloon Apparatus," *Am. J. Cardiol.*, vol. 55, pp. 1076-1083 (1985).

Fenici, R. and Melillo, G., "Biomagnetically Localizable Multipurpose Catheter And Method For MCG Guided Intracardiac Electrophysiology, Biopsy And Ablation Of Cardiac Arrhythmias," *International Journal of Cardiac Imaging*, vol. 7, pp. 207-215 (1991).

Fenici, R., et al., "Catheter Ablation Of Cardiac Arrhythmias: Magnetocardiographic Localization Of Electrocatheters And Arrhythmogenic Foci," *8th International Congress "The New Frontiers of Arrhythmias,"* Marilleva, Italy, pp. 723-731 (Jan. 31-Feb. 6, 1988).

Fenici, R., et al., "Clinical Magnetocardiography: 10 Years Experience At The Catholic University," *International Journal of Cardiac Imaging*, vol. 7, pp. 151-167 (1991).

Fenici, R. and Melillo, G., "Magnetocardiography: Ventricular Arrhythmias," *European Heart Journal*, vol. 14 (Suppl. E), pp. 53-60 (1993).

Harada, A., et al., "Potential Distribution Mapping: New Method For Precise Localization Of Intramural Septal Origin Of Ventricular Tachycardia," *Circulation*, vol. 78 (Suppl. III), No. 5, pp. III-137-III-147 (Nov. 1988).

Hauer, R., et al., "Endocardial Catheter Mapping: Validation Of A Cineradiographic Method For Accurate Localization Of Left Ventricular Sites," *Circulation*, vol. 74, No. 4, pp. 862-868 (Oct. 1986).

Hauer, R., et al., "Endocardial Catheter Mapping: Wire Skeleton Technique For Representation Of Computed Arrhythmogenic Sites Compared With Intraoperative Mapping," *Circulation*, vol. 74, No. 6, pp. 1346-1354 (Dec. 1986).

Ideker, R., et al., "A Computerized Method For The Rapid Display Of Ventricular Activation During The Intraoperative Study Of Arrhythmias," *Circulation*, vol. 59, No. 3, pp. 449-458 (Mar. 1979).

Ideker, R., et al., "Simultaneous Multichannel Cardiac Mapping Systems," *PACE*, vol. 10, pp. 281-292 (Mar.-Apr. 1987).

Ideker, R., "A Study To Evaluate The Ability Of A Multielectrode Intracavitary Probe To Determine The Site Of Origin Of Ventricular Tachycardia," *Basic Arrhythmia Laboratory, Engineering Research Center in Emerging Cardiovascular Technologies*, Duke University, pp. 1-3.

Jackman, W., et al., "New Catheter Technique For Recording Left Free-Wall Accessory Atrioventricular Pathway Activation: Identification Of Pathway Fiber Orientation," *Circulation*, vol. 78, No. 3, pp. 598-611 (Sep. 1988).

Josephson, M., *Clinical Cardiac Electrophysiology: Techniques and Interpretations*, 2nd ed., pp. 566-580, 608-615, and 770-783 (1993).

Josephson, M., et al., "Comparison Of Endocardial Catheter Mapping With Intraoperative Mapping Of Ventricular Tachycardia," *Circulation*, vol. 61, No. 2, pp. 395-404 (Feb. 1980).

Josephson, M., et al., "Role Of Catheter Mapping In Evaluation Of Ventricular Tachycardia," *Ventricular Tachycardia—Mechanisms And Management*, pp. 309-330, Mt. Kisco, NY: Futura Publishing Co. (1982).

Josephson, M., et al., "Role Of Catheter Mapping In The Preoperative Evaluation Of Ventricular Tachycardia," *American Journal of Cardiology*, vol. 40, pp. 207-220 (Jan. 1982).

Josephson, M., et al., "Ventricular Activation During Ventricular Endocardial Pacing. II. Role Of Pace-Mapping To Localize Origin Of Ventricular Tachycardia," *The American Journal of Cardiology*, vol. 50, pp. 11-22, (Jul. 1982).

Kaltenbrunner, W., et al., "Epicardial And Endocardial Mapping Of Ventricular Tachycardia In Patients With Myocardial Infarction: Is The Origin Of The Tachycardia Always Subendocardially Localized?," *Circulation*, vol. 84, No. 3, pp. 1058-1071 (Sep. 1991).

Khoury, D. and Rudy, Y., "A Model Study Of Volume Conductor Effects On Endocardial And Intracavitary Potentials," *Circulation Research*, vol. 71, No. 3, pp. 511-525 (Sep. 1992).

Khoury, D. and Rudy, Y., "Reconstruction Of Endocardial Potentials From Intracavitary Probe Potentials: A Model Study," IEEE 0276-6547/92, pp. 9-12 (1992).

Kun, S. and Peura, R., "Conductance Volumetric Model Of An Eccentrically Positioned Catheter Within A Three-Compartment Ellipsoidal Ventricle," *IEEE Transactions on Biomedical Engineering*, vol. 40, No. 6, pp. 589-592 (Jun. 1993).

Langberg, J., et al., "The Echo-Transponder Electrode Catheter: A New Method For Mapping The Left Ventricle," *Journal of the American College of Cardiology*, vol. 12, pp. 218-223 (Jul. 1988).

Laxer, C., et al., "A Graphical Display System For Animating Mapped Cardiac Potentials," *Third Annual IEEE Symposium on Computer-Based Medical Systems*, IEEE Computer Society, pp. 197-204 (1990).

Lu, S. and Eiho, S., "Compound 3-D Visualization Of Reconstructed Coronary Arteries, Left Ventricle And Aorta From Biplane X-Ray Angiograms," *Computers in Cardiology*, IEEE Computer Society Press, 0276-6547/92, pp. 535-538 (Oct. 11-14, 1992).

Macchi, E., et al., Intracavitary Mapping: An Improved Method For Locating The Site Of Origin Of Ectopic Ventricular Beats By Means Of A Mathematical Model, *IEEE Engineering in Medicine & Biology Society 10th Annual International Conference*, pp. 0187-0188 (1988).

Macchi, E., et al., "Localization Of Ventricular Ectopic Beats From Intracavitary Potential Distributions: An Inverse Model In Terms Of Sources," *IEEE Engineering in Medicine & Biology Society 11th Annual International Conference*, pp. 0191-0192 (1989).

Masse, S., et al., "A Three-Dimensional Display For Cardiac Activation Mapping," *PACE*, vol. 14, Part 1, pp. 538-545 (Apr. 1991).

Moshage, W., et al., "Biomagnetic Localization Of Ventricular Arrhythmias," *Radiology*, vol. 180, No. 3, pp. 685-692 (Sep. 1991).

Moura, L., et al., "A Microcomputer-Based Cardiac Mapping System For Recurrent Ventricular Tachycardia Surgery," *Computers in Cardiology* IEEE Computer Society Press, 0276-6547/92, pp. 431-434 (Oct. 11-14, 1992).

Pagé, P., et al., "Surgical Treatment Of Ventricular Tachycardia: Regional Cryoablation Guided By Computerized Epicardial And Endocardial Mapping," *Circulation*, vol. 80 (Suppl. I), No. 3, pp. I-124-I-134 (Sep. 1989).

Pilkington, T., et al., "Feasibility Of Estimating Endocardial Potentials From Cavity Potentials," *IEEE Ninth Annual Conference of the Engineering in Medicine and Biology Society*, IEEE, pp. 1875-1876 (1987).

Pogwizd, S. and Corr, P., "Reentrant And Nonreentrant Mechanisms Contribute To Arrhythmogenesis During Early Myocardial Ischemia: Results Using Three-Dimensional Mapping," *Circulation Research*, vol. 61, No. 3, pp. 352-371 (Sep. 1987).

Pollak, S., et al., "Intraoperative Identification Of A Radiofrequency Lesion Allowing Validation Of Catheter Mapping Of Ventricular Tachycardia With A Computerized Balloon Mapping System," *PACE*, vol. 15, pp. 854-858 (Jun. 1992).

Potratz, J., et al., "Echocardiographic Guiding Of Catheter-Electrode During Endocardial Mapping To Determine Location Of Late Fractionated Potentials In Patients With Acute Myocardial Infarction," *European Heart Journal*, vol. 12, Abstract Supplement p. 235, abstract 1242 (Aug. 1991).

Rudy, Y. and Plonsey, R., "Annotations: A Note On 'The Brody-Effect'," *J. Electrocardiology*, vol. 11, No. 1, pp. 87-90 (1978).

Rudy, Y. and Plonsey, R., "The Eccentric Spheres Model As The Basis For A Study Of The Rule Of Geometry And Inhomogeneities In Electrocardiography," *IEEE Transactions on Biomedical Engineering*, vol. BME-26, No. 7, pp. 392-399 (Jul. 1979).

Rudy, Y., et al., "The Effects Of Variations In Conductivity And Geometrical Parameters On The Electrocardiogram, Using An Eccentric Spheres Model," *Circulation Research*, vol. 44, No. 1, pp. 104-111 (Jan. 1979).

Rudy, Y. et al., "Inverse Reconstruction Of Epicardial And Endocardial Potentials: The Use Of Temporal Information," IEEE, pp. 2006-2008 (1992).

Simpson, E., et al., "Three-Dimensional Visualization Of Electrical Variables In The Ventricular Wall Of The Heart," IEEE, TH0311-1/90, pp. 190-194, (1990).

Smith, W., et al., "A Computer System for the Intraoperative Mapping of Ventricular Arrhythmias," *Computers and Biomedical Research, an International Journal*, vol. 13, No. 1, pp. 61-72 (Feb. 1980).

Smith, W. and Ideker, R., "Computer Techniques For Epicardial And Endocardial Mapping," *Progress in Cardiovascular Diseases*, vol. 26, No. 1, pp. 15-32 (Jul./Aug. 1983).

Spach, M. and Barr R., "Analysis Of Ventricular Activation And Repolarization From Intramural And Epicardial Potential Distributions For Ectopic Beats In The Intact Dog," *Circulation Research*, vol. 37, pp. 830-843 (Dec. 1975).

Stellbrink, C., et al., "Potential Of Intracardiac Ultrasonography As An Adjunct For Mapping And Ablation," *American Heart Journal*, vol. 127, No. 4, Part 2 , pp. 1095-1101 (Apr. 1994).

Taccardi, B., et al., "A New Intracavitary Probe For Detecting The Site Of Origin Of Ectopic Ventricular Beats During One Cardiac Cycle," *Circulation*, vol. 75, No. 1, pp. 272-281 (Jan. 1987).

Taccardi, B., et al., "Potential Distributions And Excitation Time Maps Recorded With High Spatial Resolution From The Entire Ventricular Surface Of Exposed Dog Hearts," *Computers in Cardiology*, IEEE Computer Society Press, 0276-6547/92, pp. 1-4 (Oct. 11-14, 1992).

Tanigawa, M., et al., "Prolonged And Fractionated Right Atrial Electrograms During Sinus Rhythm In Patients With Paroxysmal Atrial Fibrillation And Sick Sinus Node Syndrome," *Journal of the American College of Cardiology*, vol. 17, No. 2, pp. 403-408 (Feb. 1991).

Tweddell, J., et al., "Potential Mapping In Septal Tachycardia: Evaluation Of A New Intraoperative Mapping Technique," *Circulation*, vol. 80 (Suppl. I), No. 3, pp. I-97-I-108 (Sep. 1989).

Witkowski, F. and Corr P., "An Automated Simultaneous Transmural Cardiac Mapping System," *American Journal of Physiology*, vol. 247, pp. H661-H668 (1984).

Young, M., et al., "A Real-Time Data Acquisition System For The Display Of Three Dimensional Cardiac Activation Maps," *Computers in Cardiology*, IEEE Computer Society Press, 0276-6547/92, pp. 331-334 (Oct. 11-14, 1992).

Yuan, S., et al., "Localization Of Cardiac Arrhythmias: Conventional Noninvasive Methods," *International Journal of Cardiac Imaging*, vol. 7, pp. 193-205 (1991).

Kristin Clingman Spencer, "*A Feasibility Study Of Determining The Position Of An Intracavitary Multielectrode Probe Via Impedance Measurements*," Department Of Electrical Engineering In The Graduate School Of Duke University, 1991, pp. I-VII and 1-49.

Patrick Donahoe Wolf, "*Development And Evaluation Of An Algorithm To Determine Boundary Geometry And Electrode Location From Impedance Measurements*," Department Of Biomedical Engineering In The Graduate School Of Duke University, 1992, pp. I-VIII and 1-86.

"New Catheter Will Find And Treat Cardiac Arrhythmias," WPI Journal, Summer 1993, 2 pages.

P. Mendler et al., "Multichannel Recording Of Cardiac Potentials," Medical And Biological Engineering And Computing, vol. 18, No. 5, Sep. 1980, pp. 617-624.

* cited by examiner

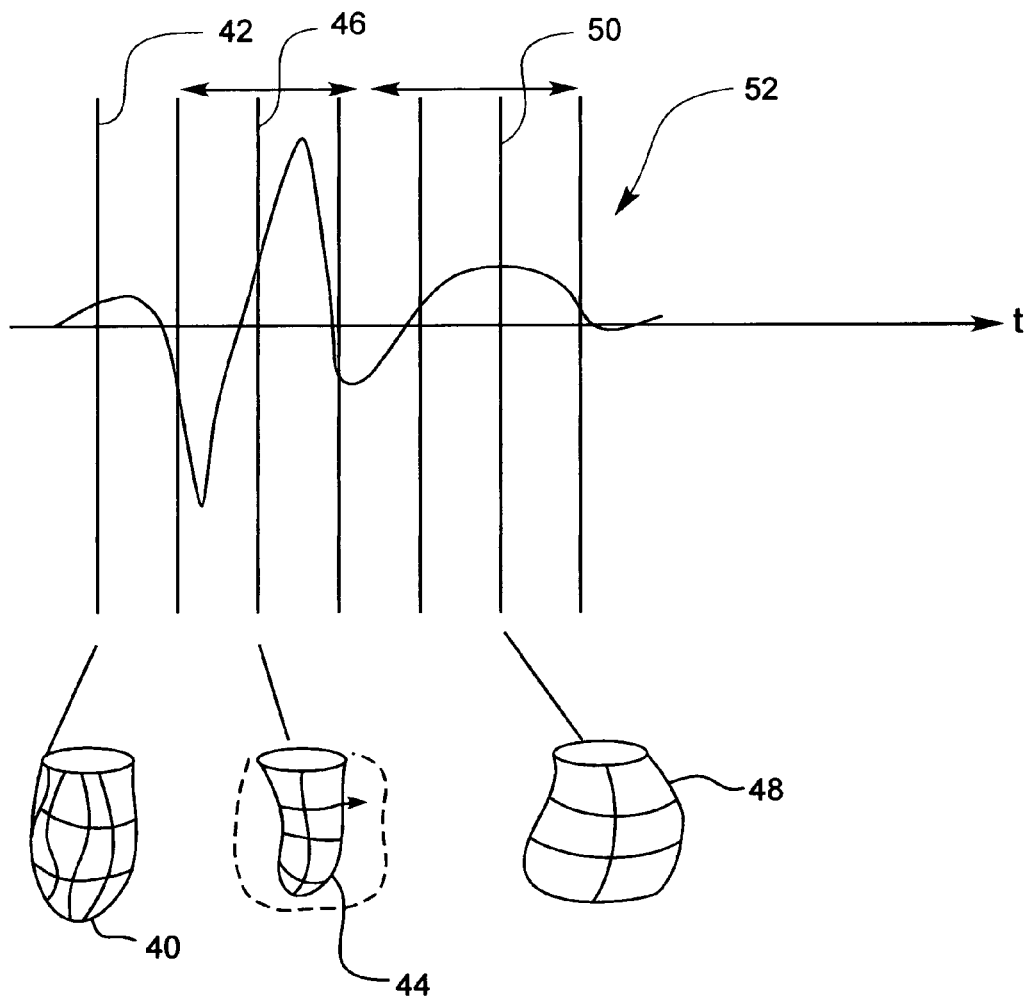

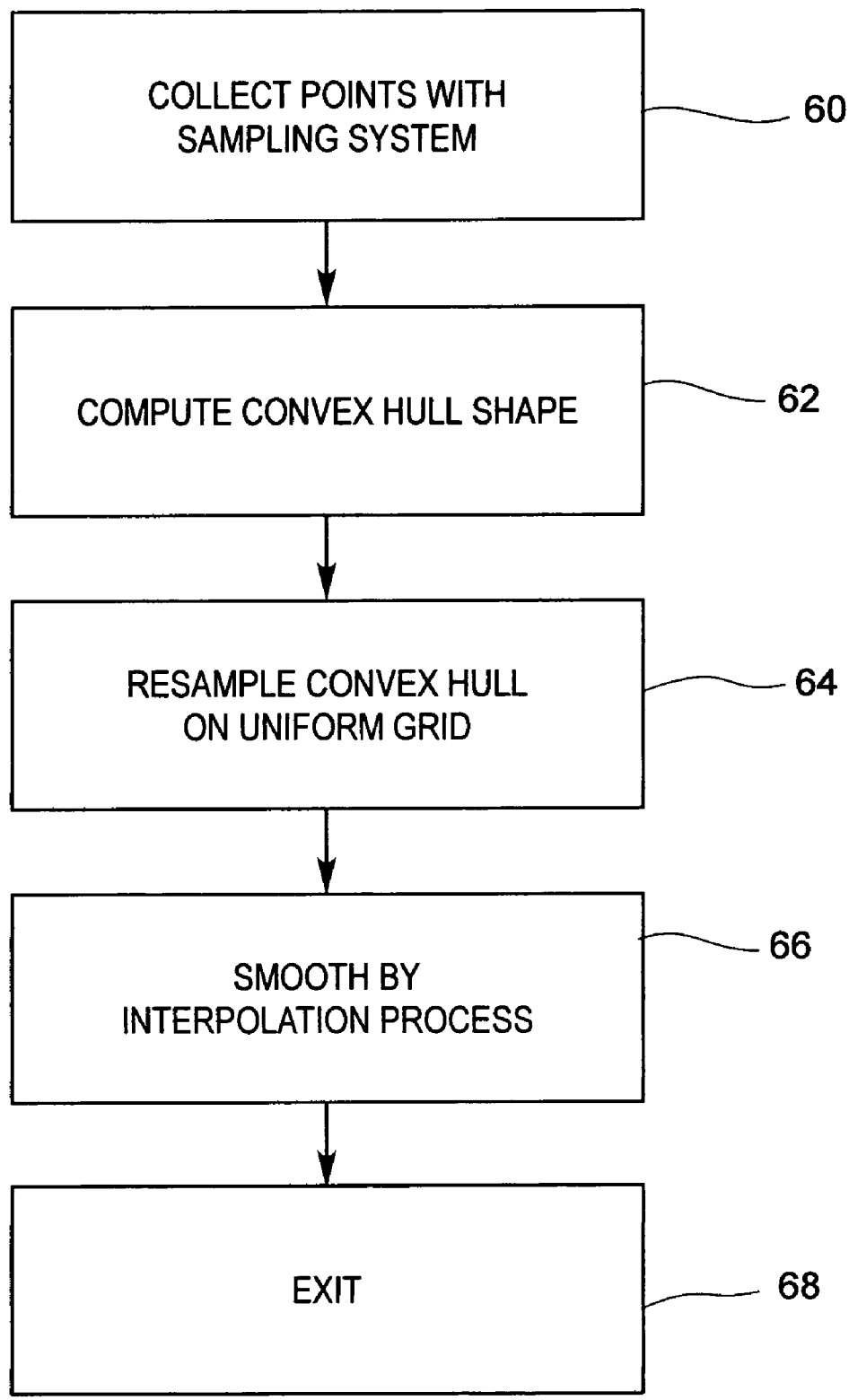

CHAMBER MAPPING SYSTEM

1. FIELD OF THE INVENTION

The present invention relates generally to the field of electro-physiology and more particularly to a system for creating a three dimensional geometric model or map of a cardiac chamber.

2. BACKGROUND OF THE INVENTION

Knowledge of the shape of a cardiac chamber is useful in a variety of medical applications. For example, it may be desirable to display electrophysiologic data on a realistically shaped cardiac surface to facilitate diagnostic procedures or to facilitate minimally invasive surgical procedures. It has been shown that the ability to present bio-potentials on such a surface provides a powerful diagnostic tool for understanding cardiac arrhythmia. Such systems are known from U.S. Pat. No. 5,553,611 and U.S. Pat. No. 5,291,549. In prior systems such knowledge is used to calibrate the system so that physical dimensions displayed to a clinician match the actual dimensions of the heart. Accurate knowledge of chamber geometry throughout the cardiac cycle may provide more computationally efficient methods for nearly real time diagnostic and/or therapeutic interventions. In this sense refined knowledge of the shape of the chamber is useful even if it is not displayed to the physician.

In general it is desirable to quickly acquire chamber geometry and there is a need to develop methods that accomplish this result in a clinical setting.

SUMMARY OF THE INVENTION

In the present invention a catheter having a "location" device is moved along the interior surface of the heart by the clinician. During this procedure the location of the catheter is monitored by a mapping system. This "tracing" process collects a relatively large set of mapping or data points. Each data and each measurement has a set of coordinates in physical space and has a time coordinate indicating where in the cardiac cycle the point was measured. It is important to note that any of several commercially available systems can be used to collect this coordinate data.

The software based computer system then builds a geometric figure in the form of a polyhedron from the data set. The convex hull methodology results in a polyhedron having triangular "panels". Conventional convex hull modeling techniques can be used to develop this initial shape. Next a resampling process occurs to "fill in" the data set in preparation for a smoothing operation. Next this convex hull shape is smoothed to represent a more physiologically realistic and computationally tractable shape for further use or display.

In use the clinician can control the "resolution" of the map by adding additional points. This map can be used in several ways. First the catheter used to "trace" the chamber may be used to deliver a therapy which may require the ability to return repeatedly to the same location in the chamber. Since wall location data can be quickly acquired it is possible to track wall motion as the heart beats. The ability to monitor wall motion provides an additional tool for diagnostic use by the clinician.

BRIEF DESCRIPTION OF THE DRAWINGS

The embodiments of the invention shown are illustrative and various modifications may be made to the invention without departing from the scope of the invention. Throughout the figures identical reference numerals refer to equivalent structure, wherein:

FIG. 6 is a sequence of smoothed chamber shapes developed during a cardiac cycle; and, FIG. 7 is a flowchart of method of carrying out the invention.

DETAILED DESCRIPTION

Knowledge of cardiac geometry is useful in a variety applications. For example in the field of electrophysiology it may be desirable to display certain information on a representation of the cardiac surface to aid diagnostic decisions. It may also be helpful to display information on a representation of the cardiac surface to guide a therapeutic intervention. Apart from display, knowledge of chamber geometry may be useful to permit calculation of other variables such as stroke volume or ejection fraction.

Various techniques have been proposed to carry out measurements of catheter location. Although the various techniques differ in detail, most systems involve the generation of a non-ionizing field in the heart and the detection of a catheter element within that field. The source of the field may be exterior of the patient or may be created within the heart itself with an appropriate catheter system. However all of these techniques generate a set of points having locations in physical space. Suitable techniques are known from the incorporated reference and U.S. Pat. No. 5,697,377 to Wittkampf.

Figure 1:
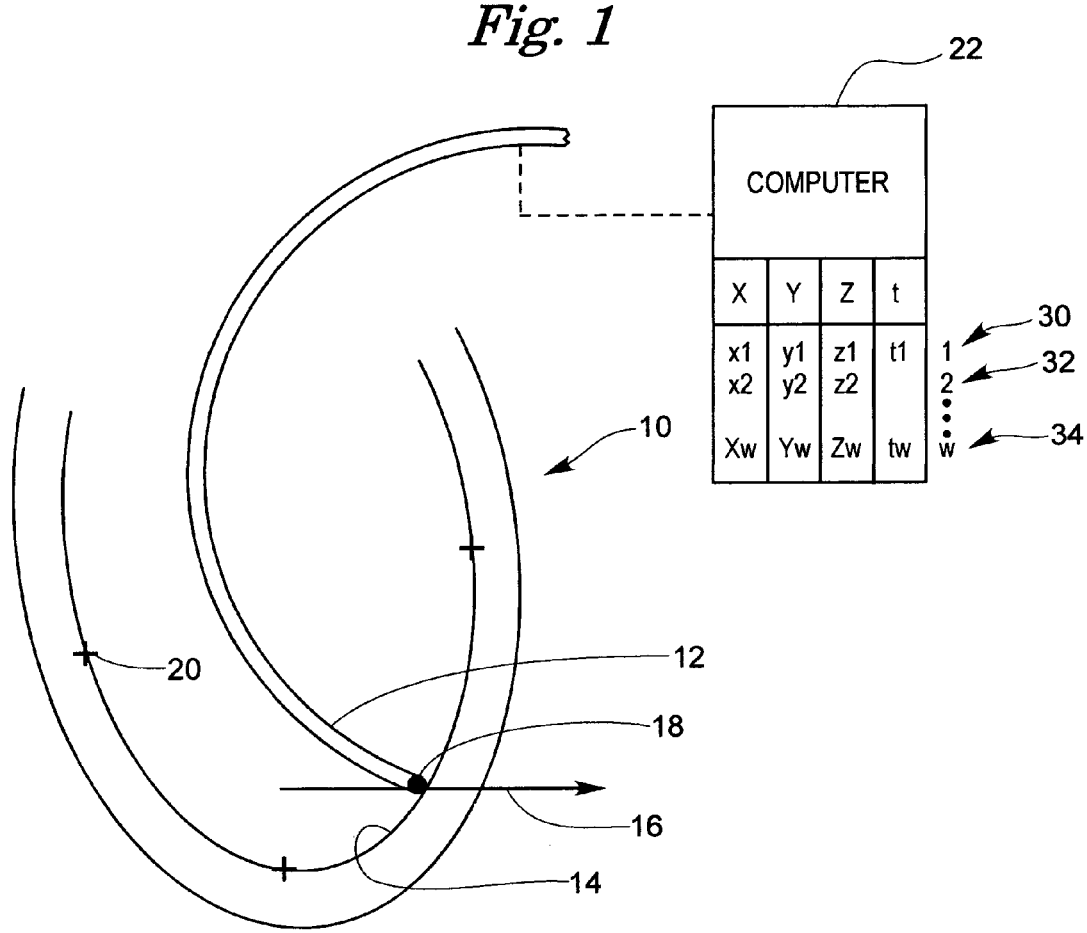
FIG. 1 is a schematic diagram of a catheter system.

FIG. 1 shows a schematic representation of a heart chamber 10 having a catheter 12 in contact with the cardiac surface 14. A field indicated by field arrow 16 creates a detectable signal at the distal element 18 of the catheter 12. The nature of the field dictates the sensor element 18. Electrical fields may be detected by electrodes, while magnetic fields may be detected by magnetic sensors.

In general the physician can manipulate the catheter 12 within the heart chamber tracing out a set of points shown by representative point 20 illustrated as a cross. The clinician may move the catheter 12 at random to develop this set of points. No pattern is implied by the distribution of points and the physician may select more or fewer locations of interest. The physical location of each measurement point in space is computed and collected by the computer system generally designated 22. At the end of the collection process each member of the set of data points has associated T, X, Y, Z values corresponding to the instant of data collection and the location of the data point in physical space. The data collection process is set forth in a table associated with the computer 22. For example the rows of data labeled 30 32 and 34 represent individual data points.

Figure 2:
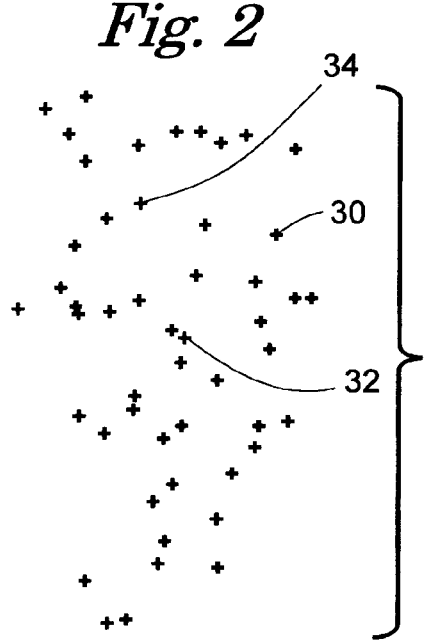
FIG. 2 is a schematic diagram of a collection of data points developed from the FIG. 1 catheter system.

FIG. 2 is a graphical representation of the results of sequential measurements made in the heart. This figure is intended to show a three dimensional cloud of data points representing the tabular data of FIG. 1. For purposes of this illustration all the data points for all of the discrete measurement periods are displayed together, with representative data points 30, 32 and 34 identified in the figure.

Figure 3:
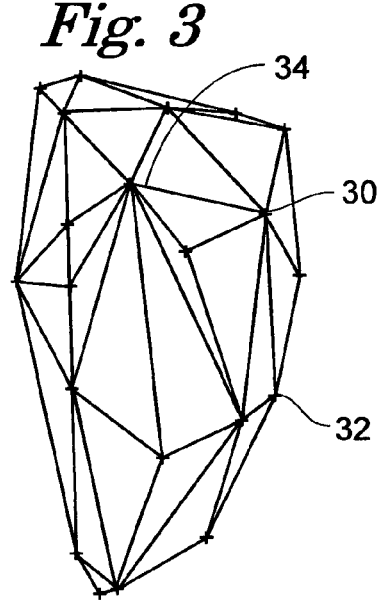
FIG. 3 is a schematic diagram of a computed convex hull heart surface.

FIG. 3 is a convex hull shape computed for the cloud of points represented in FIG. 2. This surface represents connections between the most exterior points in the data set. Usually the hull is composed of triangular panels. Convex hull algorithms are well known and publicly available software packages are available to perform this calculation, such as QHULL. See for example "The Quickhull Algorithm for Convex Hulls" by C. Bradford Barber et al. as well as the Web site at http://www.geom.umn.edu/software/qhull/.

Figure 4:
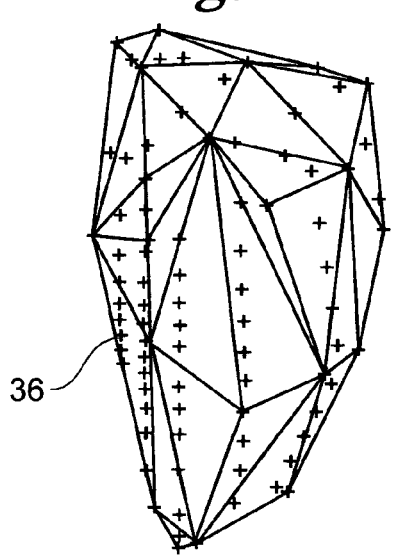
FIG. 4 is a schematic diagram of a resampled convex hull surface.

FIG. 4 shows the resampling process carried out on a regular grid to increase the number of points for further computation. The resampling process interpolates between vertices on the exterior of the polygon. In essence intermediate points are defined within each facet of the hull or polyhedron as represented by data point 38. Although the resampling process creates "fictitious" interpolated points these points are useful in the smoothing operation shown in FIG. 5.

Figure 5:
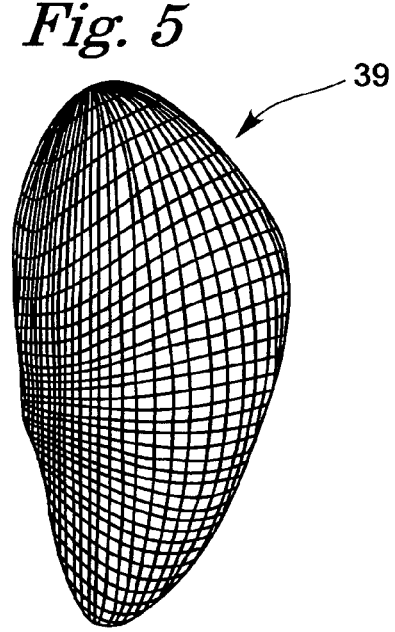
FIG. 5 is a smoothed computed heart surface.

FIG. 5 shows a smoothed shape 39 which represents a more realistic contour than the polyhedron. This surface is computed by fitting smooth curves to the enlarged or enhanced data set generated by the resampling process. Conventional smoothing algorithms are used corresponding to a least squares fit. This process yields a mathematically differentiable surface.

FIG. 6 shows the process taken at several different times in the cardiac cycle. For example chamber 40 was reconstructed at time 42, while chamber 44 was reconstructed at time 46. In a similar fashion chamber 48 is reconstructed at time 50. These times correspond to various stages of the heartbeat represented by the QRS complex 52. By tracking wall position as the heart contracts the clinician can extract diagnostic information concerning relative wall position, motion, and acceleration. Although there are numerous ways to use the sequential data, one useful technique is to construct a normal from the surface and to note the point at which it intersects a superimposed hull of greater volume. The distance between the two surfaces is calculated along the direction of the normal and this distance measurement is used to compute velocity and acceleration for the wall at that location.

FIG. 7 shows a flowchart showing an illustrative sequence fro carrying out the method of the invention. In process 60 the various data points associated with multiple endocardial locations are collected. Each point in this set has coordinates in space. In general several dozen points are collected. A larger data set results in a more complex representation of the heart; however, it is computationally more expensive.

In process 62 an algorithm is used to compute the convex hull shape. This shape estimates the boundary of the interior of the heart from the set of points. In process 64 the convex hull is resampled on a regular grid of points in physical space. By resampling the computed hull shape on the regular grid, a larger set of points is generated. Most significantly this enlarged set of points ensures that computational points are available along the length of each edge of the hull. In process 66 an algorithm is used for smoothing the convex hull shape. This process forms a mathematically differentiable shape approximating the physiologic shape of the heart chamber. Any of a number of interpolation processes can be adopted to implement this portion of the process. The final process 68 causes the model to exit to a display routine or other process where the computed shape is used for further analysis.

Although a representative illustration of the methodology is given various modifications can be made without departing from the scope of the invention.

What is claimed is:

1. A method of modeling a chamber of the heart in three-dimensions comprising:
    collecting a set of points inside the heart, each point having coordinates in three-dimensional space, forming a raw data set;
    defining an interior direction and exterior direction for said raw data set;
    selecting a first point;
    selecting at least two neighbor points from said data set that are close and more exterior than said first point, said first point and said two neighbor points forming selected data;
    forming a polygon with said selected data;
    repeating said selecting steps and said forming step forming a convex hull shape thus estimating the boundary of the heart from said raw data set.

2. The method of claim 1 wherein said collecting step is carried out over more than one cardiac cycle to create an average cardiac cycle creating a composite average of a series of heart beats.

3. The method of claim 2 wherein the composite average is measured periodically for a patient over the course of a therapy or treatment regime.

4. A method of modeling a chamber of the hear in three-dimensions comprising:
    collecting a set of points inside the heart, each point having coordinates in three dimensional space;
    defining an interior direction and exterior direction for said raw data set;
    selecting a first point;
    selecting at least two neighbor points from said data set that are close and more exterior than said first point, said first point and said two neighbor points forming selected data;
    forming a polygon with said selected data;
    repeating said selecting steps and said forming step forming a computed convex hull shape from said raw data set;
    resampling said computed convex hull shape on a regular grid to generate an enlarged set of points;
    smoothing said convex hull shape forming a mathematically differentiable shape approximating the physiologic shape of the heart chamber from said enlarged set of points.

5. The method of claim 4 wherein said collecting step further includes collecting points at a set of times synchronized with the cardiac rhythm cycle, such that said points have physical coordinates in space at a specific time in the cardiac cycle.

6. The method of claim 5 wherein said step of repeating said selecting steps and said forming step forming a computed convex hull shape is taken at discrete intervals in time corresponding to various stages of the heart cycle, generating a plurality of hull shapes.

7. The method of claim 6 further comprising the step of sequentially comparing said hull shapes to develop a measurement of cardiac wall position.

8. The method of claim 6 further comprising the step of sequentially comparing said hull shapes to develop a measurement of cardiac wall velocity.

9. The method of claim 6 further comprising the step of sequentially comparing said hull shapes to develop a measurement of cardiac wall acceleration.

10. The method of claim 5 wherein said collecting step is carried out over more than one cardiac cycle to create an average cardiac cycle creating a composite average of a series of heart beats.

11. The method of claim 10 wherein the composite average is measured periodically for a patient over the course of a therapy or treatment regime.

* * * * *

UNITED STATES PATENT AND TRADEMARK OFFICE
CERTIFICATE OF CORRECTION

| | |
|---|---|
| PATENT NO. | : 7,670,297 B1 |
| APPLICATION NO. | : 09/107371 |
| DATED | : March 2, 2010 |
| INVENTOR(S) | : John A. Hauck et al. |

It is certified that error appears in the above-identified patent and that said Letters Patent is hereby corrected as shown below:

Column 4, claim 4, line 19, kindly delete "hear" and replace with --heart--.

Column 4, claim 10, line 59, kindly delete "5" and replace with --1--.

Signed and Sealed this
Nineteenth Day of March, 2013

Teresa Stanek Rea
*Acting Director of the United States Patent and Trademark Office*